United States Patent [19]
Gajdos et al.

[11] Patent Number: 6,008,249
[45] Date of Patent: Dec. 28, 1999

[54] PHARMACEUTICAL, ORALLY APPLICABLE COMPOSITION

[75] Inventors: Benedikt Gajdos, Köln; Manfred Dürr, Bergheim-Glessen, both of Germany

[73] Assignee: Rhone-Poulenc Rorer GmbH, Cologne, Germany

[21] Appl. No.: 08/566,824

[22] Filed: Dec. 4, 1995

[30] Foreign Application Priority Data

Dec. 10, 1994 [DE] Germany ............... 44 44 051

[51] Int. Cl.$^6$ .................................. A61K 31/195
[52] U.S. Cl. ............................ 514/561; 514/159
[58] Field of Search .................... 514/561, 159

[56] References Cited

FOREIGN PATENT DOCUMENTS

| 0 636 365 A1 | 2/1995 | European Pat. Off. . |
| 749285 | 5/1956 | United Kingdom . |

*Primary Examiner*—Zohreh Fay
*Attorney, Agent, or Firm*—Proskauer Rose LLP

[57] ABSTRACT

A pharmaceutical, orally applicable composition is described, whereby the solid composition contains at least one active ingredient, at least one disintegrant, as well as at least one usual pharmaceutical additional ingredient. Furthermore said composition contains at least one ingredient that accelerates the decomposition of said composition in the mouth or in a liquid, whereby said ingredient is a water-soluble amino acid, a water-soluble amino acid derivative and/or a water-soluble amino acid salt.

14 Claims, No Drawings

PHARMACEUTICAL, ORALLY APPLICABLE COMPOSITION

The present invention concerns a pharmaceutical, orally applicable composition with the characteristics of the generic part of the main claim.

Solid, orally applicable pharmaceutical compositions that contain at least one active ingredient, at least one disintegrant, as well as at least one pharmaceutically usual additional ingredient, are known for a long time and available on the trade market. Depending on the respective active ingredient and/or the active ingredient mixture, said known compositions are used as tablets, granular powder or powder in order to prevent and/or to treat pain of all sorts, especially for the treatment of headaches, rheumatic pain, pain in the limbs, migraine, toothaches, as well as for the treatment of rheumatic affections, gout, non-rheumatic painful swellings and/or infections. In general therefore is required that the patient swallows the corresponding tablet or granular powder unchewed which is difficult with large tablets, or that the patient chews said tablet or granular powder before swallowing, which often leads to a conglutination of components of said tablet and/or granular powder in the dental and/or palatal area of the mouth. The removal of said conglutinated components causes problems and furthermore releases the active ingredient in the course of time, which after all then causes a very unpleasant taste in the mouth.

In order to avoid the above described problems with the application of said known pharmaceutical compositions, specifically produced tablets are known that inevitably decompose relatively fast in the mouth or in a corresponding liquid, so that hereby the chewing in the mouth of said known tablets that usually is also named Lyoc-tablets, can be omitted. Such specific and known pharmaceutical compositions have however the handicap that they can be slightly and undesirably damaged while being produced, while being transported or while being applied to the patient, so that also their use is correspondingly limited.

The aim of the present invention is to make disposable such an orally applicable, solid composition that on one side shows a particular high stability and on the other side decomposes very fast while being applied.

Said aim is realized, according to the invention, by a pharmaceutical composition with the distinguishing features of the patent claim 1.

The inventive pharmaceutical and orally applicable solid composition contains at least one active ingredient, at least one disintegrant, as well as at least one pharmaceutically usual additional ingredient. Furthermore said inventive composition contains at least one ingredient that accelerates the decomposition of said composition in the mouth or in a liquid, whereby said ingredient is a water-soluble amino acid, a water-soluble amino acid derivative and/or a water-soluble salt of an amino acid.

Surprisingly it was observed that said composition shows a very high decomposition rate, caused by the above indicated at least one ingredient (water-soluble amino acid, water-soluble amino acid derivative and/or a water-soluble salt of an amino acid), which means that, relatively to the time, said composition shows a high decomposition when it gets in contact with saliva (spittle) or an appropriate liquid, especially water. This again leads to a very fast decomposition (disintegration) of said inventive composition in the mouth, without being required to chew said inventive composition. Therefore there are no problems concerning said inventive composition, as there are known in connection with the compositions according to the prior art and also incorporate with such known compositions that contain a disintegrant. That means that the components of said inventive composition do not deposit in areas of the mouth that are difficult to reach and therefore do not cause an unwanted conglutination on the tongue and/or on the palate and/or in the dental area, so that correspondingly said inventive composition does not cause a bitter taste during the application of said composition in the patient's mouth, caused by the release of the active ingredient. Furthermore the above mentioned ingredient (water-soluble amino acid, water-soluble amino acid derivative and/or a water-soluble salt of an amino acid) accelerating the decomposition of said inventive composition in the mouth or in a liquid, does not deteriorate the stability of said composition, so that also said inventive composition is not undesirably damaged during its production, transport and application, so that correspondingly the complaint rate regarding said inventive composition particularly low. Also said inventive composition can be manufactured particularly low-priced by conventional manufacturing techniques, while contrarily this is not the case concerning the known and above mentioned Lyoc-tablets.

The above indicated high decomposition rate of the inventive composition is referred to a synergistic effect of the at least one disintegrant with the ingredient (water-soluble amino acid, water-soluble amino acid derivative and/or water-soluble salt of an amino acid).

Basically the inventive composition can contain each water-soluble amino acid, each water-soluble amino acid derivative and/or each water-soluble salt of an amino acid, if it is secured that the above indicated ingredients that accelerate the decomposition of said inventive composition in the mouth and/or in a liquid, are not toxic, and do not show interaction with the at least one active ingredient. It is particularly suitable, if the inventive composition contains the ingredient glycine, glycine derivative and/or a salt of glycine, that accelerate the decomposition of said inventive composition, whereby the term glycine derivative includes particularly ester, preferably of $C_1$—$C_4$—alcohols, and/or amides of glycine, preferably of $C_1$—$C_{10}$—carboxylic acids, and the term salts of glycine includes preferably water-soluble alkalisalts and/or alkaline earth salts, as well as the corresponding ammonium salts. These above described embodiments of the inventive composition that contain as ingredient glycine, a glycine derivative, a salt of glycine and/or their mixture, are toxicologically seen absolutely unobjectionable, whereby, caused by the relatively low price of the above indicated ingredients basing on glycine, the embodiment of the inventive composition is manufacturable to a particular low price.

Another embodiment of the inventive pharmaceutical composition contains such ingredients accelerating the decomposition (disintegration) of the inventive composition, additionally to above described ingredients basing on glycine, or instead of the ingredients basing on glycine, said accelerating ingredients are chosen from the group consisting of proline, hydroxy proline, lysine, the salts thereof and/or derivatives thereof. Hereby the term salts and the term derivatives include the salts and derivatives indicated above together with the glycine, whereby however concerning the proline, respectively the hydroxy proline, it is possible to correspondingly substitute the pyrrolidine-ring, particularly to halogenate it and/or to provide at the pyrrolidine-ring an additional $NH_2$-group, a $NO_2$-group and/or a $SO_3H$-group. Also one or more of the above mentioned substitutes can be arranged at the non-substituted $CH_2$-groups of the lysine.

Concerning the previous and exactly described ingredients of the inventive composition that accelerate the decomposition of the inventive composition in the mouth and/or in a liquid, it is to be noted that the inventive composition contains the ingredients in such a concentration that the composition decomposes (disintegrates) in the mouth, respectively in a chosen liquid within one second up to sixty seconds, preferably within one second up to thirty seconds.

Depending on each active ingredient and on the usual additional ingredients, as well as on the composing of said composition, the concentration of the ingredient, respectively of the ingredient-mixture varies in said composition between 1% by weight and 90% by weight, particularly between 20% by weight and 70% by weight, corresponding to the composition ready to use.

As disintegrants the inventive composition contains preferably starch, a starch derivative, cellulose, a cellulose derivative, alginic acid, an alginic acid derivative, casein, a casein derivative and/or an water-insoluble polyvinylpyrrolidone (crosspolyvidone). The above mentioned starch is particularly a corn- or a potato starch, the above mentioned starch derivative is particularly modified starch and/or sodium carboxymethyl starch, the above mentioned cellulose derivative is particularly carboxymethyl cellulose and/or sodium carboxymethyl cellulose. Furthermore, appropriate disintegrants are cross-linked casein, sodium salt of alginic acid, as well as polyvinylpyrrolidone insoluble in saliva and/or water, whereby the latter mentioned product is also available on the market under the trade name Kollidon CL and Polyplasdone XL.

Concerning the concentration of the disintegrant in the inventive composition it is to be noted that it varies between 1% by weight and 50% by weight, preferably between 3% by weight and 20% by weight corresponding to the composition ready to use (apply).

A especially favorable further development of the above described embodiment of the inventive composition provides that hereby the inventive composition contains the at least one active ingredient in the form of active ingredient particles that are proportionately dispersed in the solid composition. Such a further development of said composition has next to a perfect stability, next to a particularly fast decomposition rate, also a specifically high efficacy. One reason for this is that after the decomposition of the inventive composition the each active ingredient particle reaching the stomach, respectively the intestines (bowels), has a relatively large surface, so that they can cause correspondingly fast the desired therapeutic effects.

Concerning the active ingredient or the active ingredient mixture of the inventive composition it is to be noted that they are usual pharmaceutical active ingredients or active ingredient mixtures. Said composition preferably contains such active ingredient or active ingredient mixtures that usually are found in known anti-cancer agents, antibiotics, antipyretic agents, immunostimulators, immunosuppressants, anti-inflammatory agents, antiepileptic agents, agents for the treatment of cerebral affections, antihistamines, diuretics, hypotensors, antidiabetics, muscle relaxants, anti-ulcus agents, antidepressants, anti-allergic agents, cardiac-stimulating agents, vasodilators, anti-coagulant agents, antitussives and/or anti-cold agents as well as vitamins.

Particularly preferred in the sense of the present invention is a composition that contains an active ingredient with anti-inflammatory, anti-rheumatic or analgetic characteristics. Preferably the active ingredient or the active ingredient mixture is then synthesized on the base of a pyrazolone compound, a salicylic acid compound, a phenylbutanzone compound, a paracetamol acetaminopren compound, an anthranilic acid compound, an arylic acetic compound and/or an aryl propionic acid compound.

To the inventive pharmaceutical composition concretely belong such compositions that contain as active ingredient or active ingredient mixture, ibuprofene, ketoprofene, naproxene, tolmetine, furabiprofene, a derivative of furapro indomethacine, mefenamic acid, flufenamic acid, paracetamole, acetylsalicylic acid, alclofenac, ketoprofene, ibuprofene, and/or diclofenac-sodium, whereby the first mentioned active ingredients are found, when the inventive composition is supposed to be used as analgetic drug, and the latter mentioned four active ingredients are found in the inventive composition, when the inventive composition is used as an anti-rheumatic drug.

Concerning the concentration of the active ingredient and preferably the above mentioned active ingredients of the inventive composition is to be noted that this concentration of the active ingredient or of the active ingredient mixture varies between 1% by weight and 50% by weight, preferably between 15% by weight and 40% by weight, each corresponding to the inventive composition ready to use.

Especially then, when the inventive composition contains as an active ingredient a hydrophilic active ingredient, it is recommendable to provide said hydrophilic active ingredient with a hydrophobic coating-layer and/or to embed said hydrophilic active ingredient into a hydrophobic matrix. This embodiment of the inventive composition does not only show the already previous mentioned advantages (high decomposition rate, sufficient hardness and resistance), but also is characterized in that during the decomposition of the inventive composition in the mouth the active ingredient or the concrete active ingredient particles is and/or are prevented from forming large agglomerates by the hydrophobic coating-layer and/or the hydrophobic matrix, which would avoid the desired fine dispersion of the active ingredient. Furthermore, by such a hydrophobic coating-layer and/or hydrophobic matrix is achieved that a bitter or unpleasant taste possibly caused by the active ingredient is suppressed.

The above mentioned suppression of the bitter and/or unpleasant taste of said active ingredient can also be achieved for the reason that the inventive composition contains an active ingredient and/or an active ingredient mixture that is not provided with hydrophobic coating-layer and/or embedded into a hydrophobic matrix, but instead contains larger, previously consolidated active ingredient particles. By such a consolidation, specifically by a compression, of the active ingredient particles to larger agglomerates, the disposable surface is decreased in comparison to the actual active ingredient particles, so that correspondingly the decomposition procedure of said active ingredient in the mouth is delayed, which again suppresses an unpleasant or bitter taste.

For the above mentioned coating and/or embedding of said active ingredient and/or said active ingredient mixture in a hydrophobic matrix, basically all coating substances and/or embedding substances can be chosen, that on one side secure the unwanted hydrophobization of the active ingredient and/or the active ingredient mixture and on the other side are toxicologically unobjectionable. Heretofore especially coating-layers and/or embedding substances are considered that are chosen from the group consisting of shellac, stearic acid, gelatine, zein, gum arabic, cellulose derivatives, polymere acrylic acid derivatives and/or polymere vinylacetates. To be mentioned concretely are methylcellulose, ethylcellulose, hydroxypropylcellulose, hydroxypropylmethylcellulose, celluloseacetate-phthalate, hydroxypropylmethylcellulose-phthalate, as well as polymere acrylic acid derivatives, particularly copolymerisates from methacrylic acids and esters from methacrylic acids; acrylic acid ethyl-methacrylic acid methylester-copolymerisates; methacrylic acid-acrylic acid methylester-copolymerisates; acrylic- and methacrylic acid ester-copolymerisates with trimethylammoniummethacrylate; copolymerisates from dimethylaminomethacrylic acid and neutral methacrylic acid esters; vinylpyrrolidone-vinylacetate-copolymerisates; polyvinylacetate; polyvinylpyrrolidone as well as polyethylenglycol.

Concerning the amount of the above mentioned coating- and/or embedding substances it is to be noted that this amount of said coating- and/or embedding substances depends on the concentration of the corresponding hydrophilic active ingredient and/or the hydrophilic active ingredient mixture. The amount of said substances varies between 1% by weight and 10% by weight corresponding to the inventive composition ready to use.

Furthermore the inventive composition contains pharmaceutically usual additional ingredients, which are in particular bulkages, binders, lubricants, humectants, absorbents, antistatic substances, colouring substances and flavouring substances.

In particular the inventive composition contains pharmaceutically usual bulkages and binders, in a concentration between 0% by weight and 60% by weight. Further it contains povidone, sugar, sugar alcohols and/or polyethylenglycol in a concentration between 0% by weight and 10% by weight each, as well as an usual concentration of flavouring substances, particularly of sweetening substances and/or aromatics. The usual flavouring substances that are found in the inventive composition were in particular ascorbic acid, tartaric acid, fumaric acid and/or citric acid, preferably ascorbic acid because ascorbic acid additionally functions as vitamin C.

As already previous mentioned the inventive pharmaceutical composition is solid and exists preferably as a tablet or granular powder. However, it is of course possible to manufacture the inventive composition in the form of a relatively coarse-grained powder.

Further favourable developments of the inventive composition are indicated in the sub-claims.

The inventive composition is explained more precisely in the examples.

Hereinafter in the examples the terms consolidation, spray-drying, hydro-granulation are used.

By the term consolidation a procedure is meant in which the active ingredient and/or the active ingredient mixture is consolidated with a concrete additional ingredient and/or additional ingredient mixture mentioned in the examples, possibly by the addition of water, with an appropriate device, specifically a consolidating roller or a tablet compressor. Thereafter the concreted material is crushed and if necessary dried. Should the portion of fine grains in the said concreted material be to high, particularly under 80 μm, then said portion can be removed by being sieved.

By the term spray-drying a procedure is meant in which the active ingredient and/or the active ingredient mixture is dissolved or dispersed in water. Hereby the additional ingredients mentioned concretely in the examples, are added. Thereafter the dispersion and/or solution is dried in a spray tower in a stream of warm air with a product temperature between 30° C. and 120° C.

By the term hydrogranulation a procedure is meant in which the active ingredient and/or the active ingredient mixture is granulated in an appropriate device, particularly in a mixer and/or a fluid bed granulator, during addition of the additional ingredients mentioned in the examples.

Depending on the chosen active ingredient and the additional active ingredients the granular powder can be coated with an appropriate polymer.

When the products, submitted to the spray-drying, the hydrogranulation and the consolidation, are coated with an appropriate polymer which is in the following examples the product Eudragit E12,5, then this is marked in the following quoted examples by indicating the above mentioned product.

For the following components named in the examples with their trade names Polyplasdone XL (GAF, USA), Aspartam (Nutra Sweet), Kollidon 25 (BASF), Acesulfam K (Hoechst), and Eudragit L (Röhm), Aerosil 200 (Degussa), Biogapress 3326 (Gattefossé), the manufacturers are indicated in brackets after each component.

EXAMPLE 1

Manufacturing of a Table With the Active Ingredient Ketoprofene

A mixture containing water and

| 50 g | ketoprofene |
|---|---|
| 5 g | ethylcellulose | was granulated and dried. After the drying and the sieving of the dried granular powder over a sieve with a mesh size of 1 mm, the following components were added

| 119 g | glycine, |
|---|---|
| 10 g | Polyplasdone XL, |
| 1 g | Silica, |
| 10 g | aromatics, |
| 1 g | sodium chloride, |
| 2 g | sweetening substances and |
| 2 g | magnesium stearate. |

The homogenised mixture was compressed to tablets weighing 200 mg. The tablet that way manufactured was named tablet 1.

EXAMPLE 2

Manufacturing of a Tablet With the Active Ingredient Ibuprofene

A mixture containing water and

| 400 g | ibuprofene |
|---|---|
| 20 g | gelatine | was granulated and dried. After the sieving and the drying of the dried granular powder over a sieve with a mesh size of 1 mm, the following components were added

| 405 g | glycine, |
|---|---|
| 40 g | Polyplasdone XL, |
| 20 g | aromatics, |
| 3 g | silica, |
| 1 g | sodium chloride, |
| 2 g | sweetening substances and |
| 9 g | magnesium stearate. |

The homogenised mixture was compressed to tablets weighing 200 mg. The tablet that way manufactured was named tablet 2.

EXAMPLE 3

Manufacturing of a Tablet With the Active Ingredient Loperamide

Although loperamide is a hydrophilic active ingredient, it was renounced on the providing of said active ingredient with a hydrophobic coating-layer, caused by the concentration of said active ingredient being relatively low.

A mixture containing

| 2 g | loperamide - HCL, |
|---|---|
| 87.5 g | glycine, |
| 5 g | Polyplasdone XXL, |
| 0.3 g | silica, |
| 5 g | aromatics, |
| 1 g | sweetening substances and |
| 1 g | magnesium stearate | was manufactured. From the correspondingly homogenised mixture tablets weighing 100 mg were compressed that are named tablets 3.

EXAMPLE 4

Manufacturing of a Tablet With the Active Ingredient Acetylcysteine

A mixture containing water and

| 600 g | acetylcysteine, |
|---|---|
| 25 g | ethylcellulose | was granulated and dried. After the drying and the sieving of the dried granular powder over a sieve with a mesh size of 1 mm, the following components were added

| 490 g | glycine, |
|---|---|
| 55 g | Polyplasdone XL, |
| 1 g | Aspartam, |
| 1 g | saccharine-sodium, |
| 15 g | aromatics, |
| 3 g | silica and |
| 10 g | magnesium stearate. |

The homogenised mixture was compressed to tablets weighing 1,200 mg. The tablet that way manufactured was named tablet 4.

EXAMPLE 5

Manufacturing of a Tablet With the Active Ingredient Thyme Extract

A mixture containing water and

| 62.5 g | thyme (taim) dry extract, |
|---|---|
| 4 g | Eudragit L | was granulated and dried. After the drying and the sieving of the dried granular powder over a sieve with a mesh size of 1 mm, the following components were added

| 160 g | glycine, |
|---|---|
| 19 g | Polyplasdone XL, |
| 0.5 g | silica, |
| 10 g | aromatics, |
| 40 g | liquiritiae succus powder, |
| 1 g | sweetening substances and |
| 3 g | magnesium stearate. |

The homogenised mixture was compressed to tablets weighing 300 mg. The tablet that way manufactured was named tablet 5. The previous mentioned water can also be replaced by a non toxic solvent for Eudragit.

EXAMPLE 6

Manufacturing of a Tablet With the Active Ingredient in Form of an Extract of the *Echinacea Angustifolia*

A mixture containing water and

| 8 g | extract rad. echinaceae angustifolia, extract of root of plant |
|---|---|
| 0.8 g | methyl-hydroxypropyl-cellulose | was granulated and dried. After the drying and the sieving of the dried granular powder over a sieve with a mesh size of 1 mm, the following components were added

| 120.7 g | glycine, |
|---|---|
| 8 g | Polyplasdone XL, |
| 0.5 g | silica, |
| 8 g | aromatics, |
| 1 g | sweetening substances and |
| 3 g | magnesium stearate. |

The homogenised mixture was compressed to tablets weighing 150 mg. The tablet that way manufactured was named tablet 6.

EXAMPLE 7

Manufacturing of a Tablet With the Active Ingredient Carbocysteine

A mixture containing water and

| 375 g | carbocysteine, |
|---|---|
| 11.6 g | gelatine | was granulated and dried. After the drying and the sieving of the dried granular powder over a sieve with a mesh size of 1 mm, the following components were added

| 371.7 g | glycine, |
|---|---|
| 30 g | Polyplasdone XL, |
| 5 g | Aerosil, |
| 1 g | Aspartam powder, |
| 1.5 g | Acesulfam K, |
| 0.16 g | orange aromatic and |
| 4 g | magnesium stearate. |

The homogenised mixture was compressed to tablets weighing 810 mg. The tablet that way manufactured was named tablet 7.

EXAMPLE 8

Manufacturing of a Tablet With the Active Ingredient Paracetamol

A first mixture was manufactured containing

| 81.95 g | glycine and |
|---|---|
| 2 g | Kollidon 25. |

Furthermore a second mixture was manufactured containing

| | |
|---|---|
| 106.95 g | Rhodapap NCR (paracetamol ccated with ethylcellulose), |
| 6 g | Polyplasdone XL and |
| 1 g | Aerosil 200. |

From the components

| | |
|---|---|
| 0.2 g | Aspartam powder, |
| 0.3 g | Acesulfam-K, |
| 0.6 g | aromatic type peppermint |
| 0.2 g | sodium chloride | a third mixture was manufactured.

The first and the second mixture were mixed in an appropriate and pharmaceutically usual mixer. To this homogenised mixture the third mixture previous indicated was added and correspondingly mixed that long that a homogeneous mixture emerged.

To said homogeneous mixture consisting in said first, second and third mixture,

| | |
|---|---|
| 0.8 g | magnesium stearate | was added, whereby the magnesium stearate was sieved before over a sieve with a mesh size of 0.3 mm. After being mixed for fifty seconds the hereby emerged mixture was compressed to a tablet weighing 1,000 mg, whereby said tablet was named tablet 8.

EXAMPLE 9

Manufacturing of a Tablet With a Vitamin Mixture as Active Ingredient

A multivitamin mixture (142.8 g) consisting of

| | |
|---|---|
| 51.282 g | ascorbic acid (97.5%), |
| 15 g | nicotinamide, |
| 10 g | vitamin E acetate (50%), |
| 2 g | pyridoxine HCL, |
| 1.8 g | riboflavine, |
| 1.5 g | β-carotin, |
| 1.5 g | thiaminenitrate, |
| 0.3 g | folic acid, |
| 48.118 g | palatinite isomalt, |
| 0.5 g | Aerosil 200, |
| 4 g | Diogapress 3326 and |
| 6.8 g | ethylcellulose | was granulated and dried. After the drying and the sieving of the granular powder said sieved granular powder was mixed with a mixture containing

| | |
|---|---|
| 792.4 g | glycine and |
| 10 g | Kollidon 25. |

Furthermore a second mixture containing

| | |
|---|---|
| 50 g | Polyplasdone XL, |
| 5 g | Aerosil 200, |
| 1 g | Aspartam powder, |
| 1.5 g | Acesulfam K, |

-continued

| | |
|---|---|
| 1 g | sodium chloride, |
| 5 g | peach aromatic, |
| 2 g | citric acid and |
| 4 g | magnesium stearate | was homogeneously added. Then this mixture was compressed to a tablet weighing 1,000 mg that was named tablet 9.

EXAMPLE 10

Manufacturing of a Tablet With the Active Ingredient Acetylsalicylic Acid

A first mixture containing

| | |
|---|---|
| 85.897 kg | glycine and |
| 2 kg | Kollidan 25 | was manufactured.

From the components

| | |
|---|---|
| 105.263 kg | aspirin NCR-P (corresponds to 100 kg acetylsalicylic acid, coated with ethylcellulose), |
| 5 kg | tartaric acid, |
| 6 kg | Polyplasdone XL, |
| 0.31 kg | magnesium stearate, |
| 2.83 kg | talcum microcristalline and |
| 2.7 kg | inactive ingredients | a second mixture was manufactured, whereby first of all the magnesium stearate and the talcum were mixed manually and added only at the end to a first mixture consisting of aspirin NCR-P, tartaric acid, Polyplasdone XL and the inactive ingredients. Then the total mixture that way manufactured was compressed to a tablet weighing 1,050 mg that was named tablet 10.

EXAMPLE 11

Manufacturing of a Conventional Tablet With the Active Ingredient Aspirin

A first mixture containing

| | |
|---|---|
| 91.16 kg | sorbitol and |
| 2 kg | Kollidon 25 | was manufactured.

From the components

| | |
|---|---|
| 100 kg | crystalline aspirin (acetylsalicylic acid), |
| 5 kg | tartaric acid, |
| 6 kg | Polyplasdone XL, |
| 0.31 kg | magnesium stearate, |
| 2.83 kg | talcum microcristalline and |
| 2.7 kg | inactive ingredients | a second mixture was manufactured, whereby first of all the magnesium stearate and the talcum were mixed manually and added only at the end to a first mixture consisting of aspirin, tartaric acid, Polyplasdone XL and the inactive ingredients. Then the total mixture that way manufactured was compressed to a tablet weighing 1,050 mg that was named tablet 11.

According to the previous indicated manufacturing instructions in the examples 1–11 further tablets I–IX were correspondingly manufactured, whereby said further tablets I–IX did not contain glycine. On the contrary the glycine was replaced by a quantity of sorbitol corresponding to the quantity of glycine.

Of the tablets manufactured according to the examples 1–11 and the referent tablets I–IX that did not contain glycine, the decomposition times were measured. Heretofore a modified apparatus according to DAB 10 (German Pharmacopoeia) was used.

Said modified apparatus consisted in a rack with a sieving base comprising six cylindrical glass test-tubes. Said tubes, open at the upper end, were closed at the lower end only by stainless steel wire, so that the liquid could freely enter the tube. Said rack was constantly vertically moved up and down by a motor, whereby the speed was set that way that said rack was moved up and down 28 to 32 times per minute over a way of 50 mm to 60 mm. Hereby said rack was arranged in a 1-liter beaker, whereby said beaker was filled with 350 ml of cleaned water. Said rack was positioned that way that said tubes had left the water by reaching the extreme point of the upward movement, and by reaching the extreme point of the downward movement they had immersed in the water that deep that all tablets arranged in said tubes were wetted completely.

In each tube one tablet was arranged.

The temperature of the water was set during the measurement on a level between 36° C. and 38° C.

Then said rack was moved up and down that long till all tablets to be tested were decomposed. The decomposition time heretofore required was measured, whereby in the following table 1 the uppermost and the lowest decomposition time determined by six measurements are indicated.

TABLE 1

Decomposition times of the tablets manufactured according to the examples 1–11 as well as of the tablets I–IX (without the addition of glycine)

| tablet according to example | decomposition time in seconds |
| --- | --- |
| 1 | 8–15 |
| 2 | 6–14 |
| 3 | 3–6 |
| 4 | 10–16 |
| 5 | 8–10 |
| 6 | 6–9 |
| 7 | 9–12 |
| 8 | 8–12 |
| 9 | 12–18 |
| 10 | 3–8 |
| referenttablets | |
| 11 | 60–80 |
| I | 60–90 |
| II | 70–90 |
| III | 60–70 |
| IV | 90–120 |
| V | 90–100 |
| VI | 60–90 |
| VII | 80–90 |
| VIII | 70–90 |
| IX | 80–100 |

A taste- and acceptance-test was made with 30 persons who for several days took a trade-usual tablet (according to example 11) or an externally identical tablet-shaped remedy (according to example 10) that differed from the known remedies in the way that it contained additionally the quantity of glycine indicated in example 10. The persons could not distinguish both tablets from their exterior. Each person received the trade-usual tablet, as well as the above mentioned tablet-shaped remedy.

All the 30 persons conformably reported how pleasant and easy the use of the tablet mixed with glycine (according to example 10) was.

In particular the probationers conformably confirmed that compared to the conventional drug, the tablet mixed with glycine was regarded as extremely positive and pleasant during the use and chewing in the mouth. The typical and permanent conglutination of the known tablet and its components on the palate, teeth and gums was not observed during the application and use of the tablet mixed with glycine. Also this tablet dissolved a lot faster which was considered as very comfortable.

We claim:

1. A pharmaceutical, orally applicable solid composition, wherein said solid composition contains at least one active ingredient, at least one disintegrant selected from the group consisting of starch, a starch derivative, cellulose, a cellulose derivative, alginic acid, an alginic acid derivative, casein, a caesein derivative, an insoluble polyvinylpyrrolidone, and mixtures thereof, at least one usual pharmaceutical additional ingredient, and at least one ingredient accelerating the decomposition of said composition in the mouth or in a liquid, wherein said ingredient accelerating the decomposition is selected from the group consisting of a water-soluble amino acid, a water-soluble amino acid derivative and a water-soluble salt of an amino acid, and wherein said composition decomposes in the mouth or in a liquid within one to thirty seconds.

2. The pharmaceutical composition according to claim 1, wherein said ingredient accelerating the decomposition in the mouth or in a liquid is selected from the group consisting of glycine, a glycine derivative and a glycine salt.

3. The pharmaceutical composition according to claim 1, wherein said ingredient accelerating the decomposition in the mouth or in a liquid is selected from the group consisting of proline, hydroxy proline, lysine, and the salts and derivatives thereof.

4. The pharmaceutical composition according to claim 1, wherein said composition contains said ingredient accelerating the decomposition in the mouth or in a liquid in a concentration between 1% by weight and 90% by weight, relative to said composition ready to use.

5. The pharmaceutical composition according to claim 1, wherein said composition contains said disintegrant in a concentration between 1% by weight and 50% by weight, relative to said composition ready to use.

6. The pharmaceutical composition according to claim 1, wherein said composition contains said active ingredient as active ingredient particles uniformly dispersed in said solid composition.

7. The pharmaceutical composition according to claim 1, wherein said active ingredient is selected from the group consisting of an analgesic and an antirheumatic agent.

8. The pharmaceutical composition according to claim 7, wherein said active ingredient is selected from the group consisting of a pyrazolone compound, a salicylic acid compound, a phenylbutazone compound, an anthranilic acetic compound, an aryl-acetic compound and an aryl-propionic acid compound.

9. The pharmaceutical composition according to claim 7, wherein said active ingredient is selected from the group consisting of paracetamol, acetylsalicylic acid, ketoprofene, ibuprofene and diclofenac-sodium.

10. The pharmaceutical composition according to claim 1, wherein said composition contains the active ingredient in a concentration between 1% by weight and 50% by weight, relative to the composition ready to use.

11. The pharmaceutical composition according to claim 1, wherein said composition contains at least one hydrophilic active ingredient provided with a hydrophobic coating layer and/or at least one hydrophilic active ingredient being embedded in a hydrophilic matrix.

12. The pharmaceutical composition according to claim 11, wherein each of said hydrophobic coating layer and/or said matrix is selected from the group consisting of shellac, stearic acid, gelatine, zein, gum arabic, cellulose derivatives, polymeric acrylic acid derivatives and polymeric vinylacetates.

13. The pharmaceutical composition according to claim 1, wherein said solid composition contains as an additional ingredient between 0% by weight and 60% by weight bulkages and/or binders, between 0% by weight and 10% by weight of at least one substance selected from the group consisting of povidone, sugar, sugar alcohols, polyethylenglycol, sweetening agents and aromatics.

14. The pharmaceutical composition according to claim 1, wherein said composition is a tablet or a granular powder.

* * * * *